United States Patent [19]
Madsen et al.

[11] Patent Number: 5,372,142
[45] Date of Patent: Dec. 13, 1994

[54] COCHLEAR RESPONSE AUDIOMETER

[75] Inventors: Poul B. Madsen, Mississauga; Hans Kunov, Toronto, both of Canada

[73] Assignee: Poul Madsen Medical Devices Ltd., Mississauga, Canada

[21] Appl. No.: 18,521

[22] Filed: Feb. 17, 1993

[51] Int. Cl.$^5$ ............................................. A61B 5/00
[52] U.S. Cl. ..................................... 128/739; 128/746
[58] Field of Search ........ 128/739, 746, 740, 897–898

[56] References Cited

U.S. PATENT DOCUMENTS

| | | | |
|---|---|---|---|
| 4,485,823 | 12/1984 | Yamaguchi et al. | 128/739 |
| 4,809,708 | 3/1989 | Geisler et al. | 128/739 X |
| 4,848,358 | 7/1989 | Nitzan et al. | 128/740 |

FOREIGN PATENT DOCUMENTS

| | | | |
|---|---|---|---|
| 0225045 | 7/1985 | Germany | 128/739 |
| 0227588 | 9/1985 | Germany | 128/746 |
| 0488584 | 1/1976 | U.S.S.R. | 128/746 |
| 0959754 | 9/1982 | U.S.S.R. | 128/746 |

Primary Examiner—Angela D. Sykes
Attorney, Agent, or Firm—R. Craig Armstrong

[57] ABSTRACT

The invention provides a cochlear response audiometer, and new methods for signal generation, detection and processing. The invention preferably uses bone conducted sound, applied to the mastoid, forehead, or any other place with good mechanical contact to the skull, via a vibrator. The bone conducted sound stimulates the cochlea via the skull. The stimulus also produces a sound in the ear canal, but at a very low level, so there is no high level stimulus signal and ringing travelling toward the cochlea at the same time as the cochlear response is travelling back into the ear canal. The responses from the cochlea are recorded, preferably by using a differential amplifier input circuit for the microphone when air-borne response signals are used, and the responses are processed in a way which compensates for the stimulus artefact, by subtracting a scaled-down version of the cochlear response to a large stimulus from the cochlear response to a moderate stimulus.

13 Claims, 2 Drawing Sheets

COCHLEAR RESPONSE AUDIOMETER

BACKGROUND OF THE INVENTION

1. Field of the Invention

This invention relates to cochlear response instrumentation, and to improved techniques for stimulating, recording and processing cochlear responses (acoustic sounds emanating from the inner ear).

Cochlear response audiometers are used for the purpose of research into the physiology of the inner ear and for assistance in diagnosing and screening such conditions as noise-induced hearing loss and sensori-neural hearing loss in infants as well as adults.

2. Description of the Prior Art

Existing cochlear emission instrumentation and related problems can be described as follows.

The following comments are based on the use of Otodynamics instrument model ILO88, as well as information and the description in Peter John Bray's thesis "Click evoked otoacoustic emission and the development of a clinical otoacoustic hearing instrument", University College and Middlesex School of Medicine, London (UK), June 1989. The Abstract of the Disclosure of a United States patent relating to the instrument, U.S. Pat. No. 4,374,526 (David T. Kemp, granted May 17, 1983), states:

"A hearing faculty test and apparatus therefor is based on the finding that sound input to the ear gives rise to a returned wave from and related to the condition of the inner ear, this wave being detectable as an echo from the ear drum. The apparatus preferably comprises a sealing aural probe housing transducers respectively to project a repetitive transient sound by pulse generator activation and to pick-up for detection successive echoes by time-gating. Detected echoes are preferably averaged during processing for display. The echo occurs about 5-20 ms after its sound and a maximum operating frequency of about 50 Hz is appropriate. A continuous sound input can be used with consequent echo interference detectable as rapid changes of acoustic impedance with sound input frequency. Another alternative can involve detection of the ear drum movement by returned waves."

The ILO88 device, which is based on the above patent, uses 80 μs clicks as stimulation. The peak Sound Pressure Level ("SPL") in the ear canal is 80-85 dB. These high levels, compared to the emission levels of 0-20 dB, create problems in the sensitive preamplifier as well as in the signal storage section. To compensate for the problem, the stimuli are presented in the form of click trains, each containing 4 stimuli, as shown in FIG. 1. The first 3 stimuli are positive with a certain amplitude (1.67 V), and the fourth is negative with an amplitude 3 times the amplitude of the positive-going stimuli (5.0 V). This way, the stimulus artefacts are partly cancelled, as well as some of the responses from the cochlea. For this reason, the first 4 ms of the response are not displayed. Another problem is that the ringing (i.e., the direct after-effect) from a brief 80 dB SPL signal in the ear canal could still be at a level where it interferes with the cochlear emission, especially at higher frequencies, where the delay of the emission is short (1–5 ms).

In the clinic, there are a few serious problems. One problem is that it is very difficult to fit the probe properly, especially in babies and infants. This is mainly due to the way the probe is designed, the availability of ear tips for a good seal, as well as the acoustic noise introduced into the probe when the probe cord is touched. If environmental noise is too high (e.g. due to air conditioning), then it is very difficult to perform a test. If the patient's hearing loss is higher than 20–25 dB, then no emission can be measured.

SUMMARY OF THE INVENTION

One object of the invention is therefore to provide an improved cochlear response audiometer which attempts to overcome some of the above-mentioned deficiencies. Another object is to provide new methods for signal generation, detection and processing.

Recognizing the difficulties with the ILO88, new ways were therefore sought to eliminate some of the problems.

One main difference between the ILO88 and the present invention is the way the stimulus is presented. The ILO88 stimulates the cochlea using air borne sound through the ear canal, ear drum, ossicular chain and oval window into the cochlea. The stimulus Sound Pressure Level required to elicit an emission is relatively high.

By contrast, the present invention preferably uses bone conducted sound, applied to the mastoid, forehead, or any other place with good mechanical contact to the skull via a vibrator such as a standard bone conductor ("BC"). The bone conducted sound stimulates the cochlea via the skull. The stimulus also produces a sound in the ear canal, but at a very low level.

It is assumed that the excellent results using bone conduction as stimuli are due to the fact that only low sound pressure levels are created in the ear canal: there is no high level stimulus signal and ringing travelling toward the cochlea at the same time as the cochlear response is travelling back into the ear canal. Another advantage is that the preamplifier is not overloaded as the stimulus signal in the ear canal is low.

The preferred embodiment of the invention involves: Stimulation of the cochlear emission by vibrating the skull (bone conduction); recording the responses from the cochleae by the vibrations generated by the cochleae in the skull and/or the ear canal; using a differential amplifier input circuit for the microphone used in recording the responses, when air-borne response signals are used; and processing the responses in a way which compensates for the stimulus artefact.

Another aspect of the invention relates to the definition of stimulus signals and analysis techniques.

The invention significantly improves the performance of otoacoustic emission test equipment.

Further features of the invention will be described or will become apparent in the course of the following detailed description.

BRIEF DESCRIPTION OF THE DRAWINGS

In order that the invention may be more clearly understood, the preferred embodiments thereof will now be described in detail by way of examples, with reference to the accompanying drawings, in which.

DETAILED DESCRIPTION OF THE PREFERRED EMBODIMENT

In the invention, stimulation by mechanical vibration of the skull preferably is employed. The cochlea is part of the temporal bone, which is a part of the skull. Thus, the cochlea is mechanically tightly coupled to the rest of the skull, and vibrations set up anywhere in the skull propagate to both cochleae. In the case of neonatals, the entire skull may not be a single mechanical unit, and stimulation may be confined to the part of the skull containing the cochlea to be tested. In practice, the transducer is placed on top of the skin covering the skull. Alternatively, it can be placed in contact with the subject's teeth. A certain force must be applied to the transducer to secure a good acoustic contact to the skull.

Mechanical vibrations of the skull may also be employed for pick-up of cochlear responses whether the stimulus is presented via the skull or teeth, or in the ear canal. Cochlear emissions are transmitted from the cochlea to the skull. Thus, the responses can be detected by a sensitive mechanical pickup placed on the skull or in contact with the teeth. In practice, the transducer is placed on top of the skin covering the skull, using a certain force.

Figure 2:
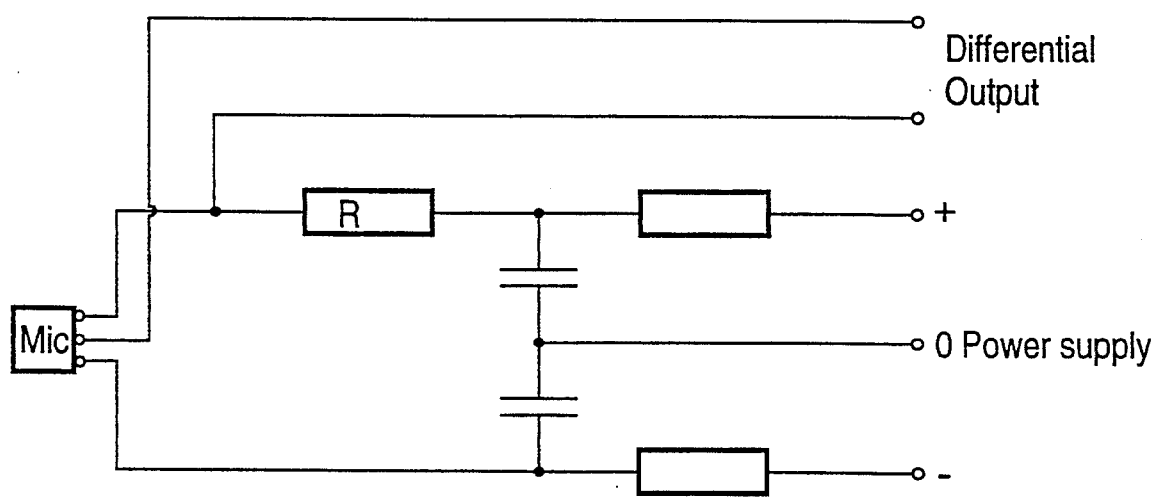
FIG. 2 is an illustration of a microphone circuit for use in the present invention.

A differential output microphone circuit preferably is employed. Normally, miniature electret microphones have single-ended outputs. This is adequate in most applications, but creates problems when extremely low-level signals are to be measured, such as is the case with cochlear emissions. In the present invention, therefore, an electret microphone having a built-in FET transistor with a resistor in either the drain or the source is employed. By supplying an external matched resistor, as shown in FIG. 2, it is possible to obtain a differential output from the circuit.

The primary advantage of using such a differential output is a reduction in electrical interference from external sources.

Figure 1:
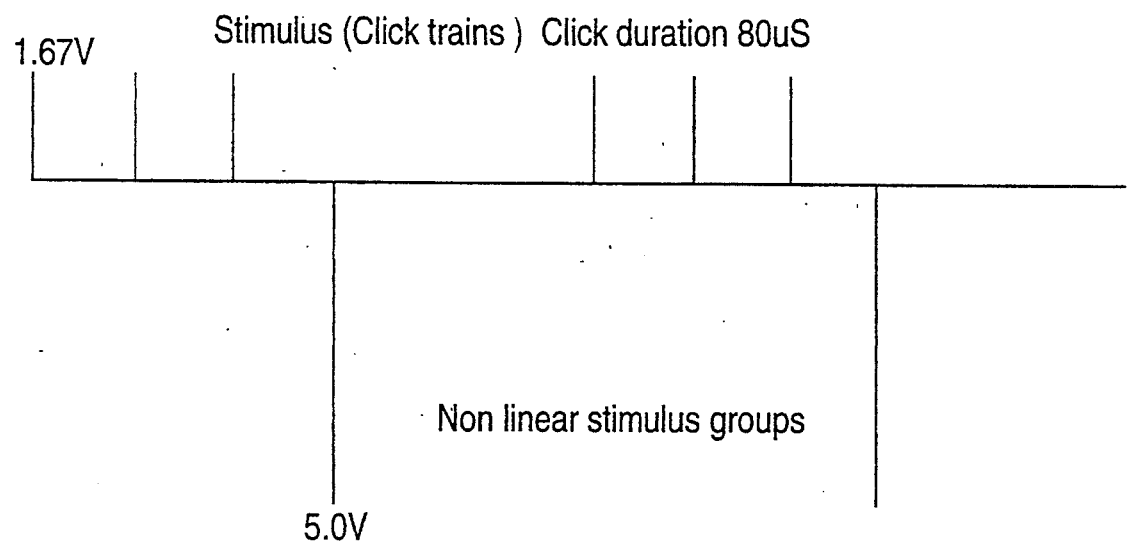
FIG. 1 is a representation of the stimulus signal used in the ILO88 (prior art)

In processing the responses, a novel means of compensating for stimulus artefacts preferably is also employed. Earlier attempts to compensate for the stimulus artefact consist of exploiting the non-linear response of the normal cochlea (as in the ILO88, FIG. 1). In theory, then, three positive-going stimuli of magnitude A, followed by one of amplitude $-3A$ are added. Supposedly, the artefacts practically cancel. The assumption that the artefacts will add up to zero does not hold true in practice, however.

In this invention, the preferred method of compensation is different. When a stimulus of a high level is presented to the ear (regardless of the stimulus signal path, i.e. bone/teeth or ear canal), the artefact can be seen on the pick-up transducer along with the response. However, the level of the response is vanishingly small in comparison with the stimulus artefact. Initially, a high-level stimulus signal is imposed on the ear. The measured artefact, assuming that it is a linear function of the stimulus, can then be used in subsequent recordings by subtracting a scaled-down version of it from the response. It is a reasonable assumption that the cochlear response reaches a plateau at a certain stimulus level. If the initial stimulus is well above that level, the subtraction will yield an artefact-free response.

Figure 3:
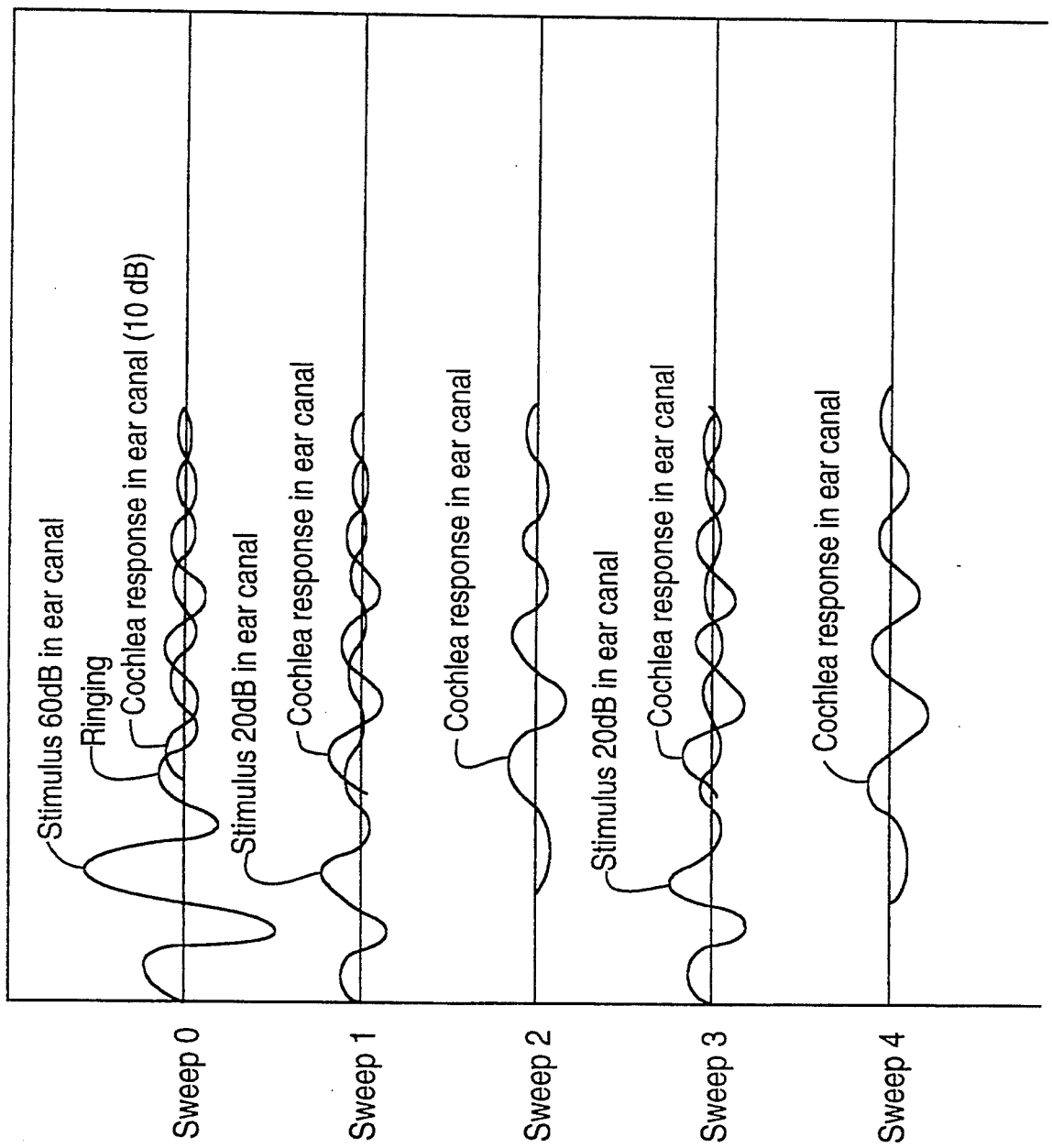
FIG. 3 is an illustration of the preferred stimulus artefact and cochlear response signals.

In order to eliminate the stimulus artefact in the measurements and display, the following therefore is suggested. The stimulus (tone pips) is adjusted so that a high level SPL, e.g. 60 dB, is created in the ear canal. Five sweeps are run and the average is stored in memory No. 2. This signal contains the stimulus signal as well as the associated cochlear emission (see FIG. 3 sweep 0).

The actual test is then started (it is assumed here that a normal-hearing subject is being tested), and the stimulus level is adjusted so that a level of 20 dB SPL is created in the ear canal. Sweep no. 1 is run and the result is stored in memory No. 1. The result contains the stimulus artefact as well as the associated cochlear emission. The stimulus signal was attenuated 40 dB going from sweep 0 to sweep 1.

Sweep no. 2 takes the stimulus signal stored in memory No. 2, attenuates it by 40 dB, makes a phase reversal and applies this signal to memory No. 1. The stored signal in memory No. 2 contained both the stimulus signal and the cochlear response. As the signal in memory No. 2 is attenuated by 40 dB, the influence of the cochlear response is so small that it is without influence on the result. In this way, the stimulus artefact in memory No. 1 has been cancelled.

The measurement continues in sweep 3 and the result is stored in memory No. 1 in the same way as sweep no. 1. Sweep no. 4 is handled the same way as sweep no. 2.

The number of sweeps needed depends on the stimulus level. The closer one gets to threshold, the more sweeps are required. At threshold, 500 to 1000 sweeps are needed, but at levels of 10–20 dB above threshold, 200–500 sweeps are sufficient. The repetition rate can be up to 50/sec.

If a BC stimulus is applied to the forehead, both left and right ears can be tested at the same time by applying a pick-up probe to each ear. The instrument can be designed in such a way that it automatically tests a subject.

In conventional audiometry, 10 frequencies in the range from 125–8000 Hz are normally used. At this time it is not known what cochlear responses can be expected below 500 Hz and above 4–6 kHz. One of the problems in achieving high frequency measurements is to find suitable transducers, mainly for BC. A computer can be programmed to automatically go through the frequency range, as well as threshold detection, and determine the number of sweeps needed.

A variation on the above involves the use of so-called "distortion product cochlear emission audiometry", where two continuous sinusoidal (pure) tones are simultaneously presented, and a distortion product, such as $2f_1 - f_2$ is detected by a probe in the ear canal or by some other means. The inventors propose to use frequencies $f_1$ and $f_2$ which are phase-locked. Thus, there is a simple relationship between the two frequencies: $n\ f_1 = m\ f_2$, where m and n are integers. When this is true, the stimulus pattern will repeat itself with a period of $m/f_1 = n/f_2$. The following two points assume that the cochlear responses are at least partly phase-locked (at least in the short term, for a few hundred milliseconds) to the stimulus signal. For simplicity's sake, it can be assumed that the two stimulus signals both cross zero at $t_0=0$, $t_1=m/f_1$, $t_2=2m/f_1$, etc.:

1. The response from the cochlea can be time-averaged, before a spectral analysis or other processing takes place, by locking the time averaging to the times $t_0, t_1, t_2$, etc. Previously, the normal procedure was Fast Fourier Transformation of the raw signal.

2. The phase of the response relative to the stimulus can be recorded and used for diagnostic purposes.

This part of the invention includes three aspects: (1) An optimum choice of frequencies for distortion product measurements, and (2) detection of distortion products, and (3) swept frequency distortion product audiometry.

With respect to the optimum choice of frequencies for distortion product measurements, cubic distortion product measurements in the ear and elsewhere often make use of the intermodulation frequency product $2f_1 - f_2$, where $f_1$ and $f_2$ are the primary, man-made stimulation frequencies, and $2f_1 - f_2$ is a result of the nonlinearity in the object upon which the primaries have been impressed.

In the case of otoacoustic distortion products, the ratio between $f_1$ and $f_2$ of between 1:1.2 and 1:1.3 is often recommended. In practice, to secure a distortion product with a frequency between zero and the lowest primary frequency ($f_1$), the ratio must be between 1:1 and 1:2.

The distortion product can be measured with digital techniques, such as the Fast Fourier Transform (FFT), but other methods as well. In all the digital techniques, the results will be much better when the analysis window contains exactly an integral number of periods of the signals under study. When this is the case, sidebands due to truncation or windowing are eliminated.

One aspect of the invention therefore deals with a method of choosing the relative frequencies for a stimulus signal where a brief burst of two frequencies is to be presented. It is well suited for cubic distortion measurements, but has other applications as well. That aspect involves the choice of primary signal frequencies $f_1$ and $f_2$, and a time interval T, here called an "elemental time window", such that $f_1 = a/T$, $f_2 = b/T$, where a and b are integers, and T is the elemental time window width in seconds.

To illustrate this, the example of $a=4$, $b=5$, and $T=5$ milliseconds can be used. In this special case, $f_1 = 800$ Hz, $f_2 = 1000$ Hz. If interested in the cubic distortion product, its frequency is $2f_1 - f_2 = 600$ Hz.

Another aspect of the invention involves a stimulus signal (the primaries) represented in a window of exactly nT seconds, where n is an integer. Within this window, the stimulus is given by $x(t) = A \{\sin(2\pi at/T) - B \sin(2\pi bt/T)\}$.

With this choice, the window will contain exactly na periods of the signal with frequency $f_1$, nb periods of the signal with frequency $f_2$. If the beginning of the window is at $t=0$, the signal starts at a zero-crossing with minimal slope. Because the number (2a-b) is an integer, there is also an integral number of periods of the cubic distortion product signal with frequency $2f_1 - f_2$.

Preferably, $B = a/b$. This condition leads to slopes of zero at zero-crossings once per elemental time window. If those times are chosen as the truncations of the stimulus signal it has a smooth continuation to the zero-signal segments before and after. In the example above, the stimulus signal could be $x(t) = 5 \sin(2\pi 400t) - 4 \sin(2\pi 500t)$, $0 < t < 10$ ms, etc.

Preferably, the stimulus signal is represented in the elemental time window by mab(2a-b) discrete samples, where m is an integer. The number ab(2a-b) is an integer which is equal to the product of the number of periods in the elemental window of the following three signals: the two primary frequencies, and the cubic distortion product. This choice of number of samples leads to computational simplicity and very high accuracy in calculations.

As an alternative to Fast Fourier Transforms, a digital method of determining these cubic distortion products may be used, in which the response signal (consisting of primaries, their harmonies and intermodulation products, and noise) is independently multiplied by two sinusoidal signals, each at the same frequency as the cubic distortion product, i.e., (2a-b)/T, but phase shifted by 90 degrees from one another.

This digital method of detecting cubic distortion products is based on the windowed representation of the stimulus signal mentioned above. Within each window (consisting of any integral number of elemental windows), the response signal is multiplied, and the result of the multiplication integrated. It can be shown, that after the integration, the only components that will give a contribution are the cubic distortion products. There will also be some contribution from any noise signal with frequency components near the cubic distortion product frequency, but in most cases the noise will be random and by using sequential windows, the effect can be reduced or eliminated.

In the example, the frequency of the distortion product is 600 Hz, and the two signals would be, $x(t) = C \sin(2\pi 600 t)$, and $x(t) = C \cos(2\pi 600 t)$, where C is an arbitrary amplitude.

This method allows for simple determination of the distortion product, because the integral of the product, within the window, will be zero for any of the primaries and their harmonics.

Preferably, as a method for the measurement of the phase of the distortion product, the phase angle of the cubic distortion product can be found as $\phi = \arctan(\alpha/\beta)$, where $\alpha$ and $\beta$ are the results of the integration of the results of the multiplications above.

The method provides the possibility of determining the phase angle of the distortion product. In complex systems, such as the inner ear, this will most likely have clinical significance.

With respect to swept frequency distortion product audiometry, in distortion product cochlear response audiometry it is common practice to identify a nominal measurement frequency as the geometric mean of the two primary frequencies, i.e., $f_0 = \sqrt{(800 \cdot 1000)} = 894.43$ Hz. By adjusting the elemental time window T, any nominal frequency $f_0$ can be produced. For a given ratio of primary frequencies, i.e., for a given set of a and b, the easiest way to change the nominal frequency is to change the rate with which the mab(2a-b) samples of the stimulus signal are converted into an analog signal. In practice, this adjustment can be made very quickly electronically.

One embodiment of the invention therefore involves a method of measuring cubic distortion products by sweeping the nominal $f_0$ over the frequency range of interest. This is achieved by presenting sequential windows with stimulus signals in the form described above. A number of measurements on a given window/frequency combination is performed until a satisfactory outcome has been determined, after which the window/frequency is automatically set to the next predetermined nominal values.

The advantage of this method is the very high speed with which it may be possible to complete distortion product measurements over a large frequency range.

It will be appreciated that the above description relates to the preferred embodiment by way of example only. Many variations on the invention will be obvious to those knowledgeable in the field, and such obvious variations are within the scope of the invention as described and claimed, whether or not expressly described.

What is claimed as the invention is:

1. A method for eliciting and recording cochlear responses of a subject, comprising the steps of applying a stimulus signal by mechanically vibrating the subject's teeth or the bony structure of the subject's head, without using either ear canal to apply said stimulus signal, and electronically recording the cochlear responses to said stimulus signal and electronically isolating said cochlear responses from other responses.

2. A method as recited in claim 1, wherein said recording of the cochlear responses involves recording the mechanical vibrations from the teeth or from the bony structure of the subject's head.

3. A method as recited in claim 1, wherein said recording of the cochlear responses is by means of a microphone positioned in the subject's ear canal.

4. A method as recited in claim 3, wherein said microphone is connected to a differential amplifier input circuit.

5. A method for eliciting and recording cochlear responses of a subject, comprising the steps of applying a stimulus signal by mechanically vibrating the teeth or by mechanically vibrating the bony structure of the subject's head or by sending an airborne signal into an ear canal of the subject, and recording the cochlear responses to said stimulus signal, wherein said stimulus signal has a pair of phase-locked frequencies $f_1$ and $f_2$, and an elemental time window T, such that $f_1 = a/T$ and $f_2 = b/T$, where a and b are integers, and T is the elemental time window width in seconds.

6. A method as recited in claim 5, where said stimulus signal is presented in a window of exactly nT seconds, where n is an integer, said stimulus signal within said window being given by $x(t) = A \{\sin(2\pi at/T) - B \sin(2\pi bt/T)\}$, where A is the amplitude of the stimulus signal and B is the relative amplitude between the frequencies.

7. A method as recited in claim 6, where presentation of the stimulus signal in the elemental time window is defined by mab(2a−b) discrete samples, where m is an integer.

8. A method as recited in claim 6, in which the response signal comprising primaries, their harmonics and intermodulation products, and noise, is independently multiplied by two sinusoidal signals each having a frequency of (2a−b)/T and phase shifted by 90 degrees from one another, the method allowing the detection of a cubic distortion product signal.

9. A method as recited in claim 8, where a phase angle $\phi$ for the cubic distortion product signal is measured using $\phi = \arctan(\alpha/\beta)$, where $\alpha$ and $\beta$ are the results of the integration of the results of the two multiplications in claim 21.

10. A method as recited in claim 6, wherein a stimulus signal having a nominal frequency $f_0$ (a geometric mean of $f_1$ and $f_2$) is swept over a frequency range of interest, sequential windows being presented with said stimulus signal, a number of measurements being performed on a given window/frequency combination until a satisfactory outcome has been determined and the window/frequency combination being then automatically set to another predetermined value.

11. A method as recited in claim 5, where B is a/b.

12. A method for eliciting and recording cochlear responses of a subject, comprising the steps of applying a stimulus signal by mechanically vibrating the teeth or bony structure of the subject's head or by sending an airborne signal into an ear canal of the subject, recording the cochlear responses to said stimulus signal, and reducing a stimulus artefact by subtracting a scaled-down version of the cochlear response to a large stimulus from the cochlear response to a moderate stimulus that is smaller than the large stimulus.

13. A method for eliciting and recording cochlear responses of a subject, comprising the steps of applying a stimulus signal to the cochlea, recording the responses to said stimulus signal by recording the mechanical vibrations from the teeth or bony structure of the subject's head; and electronically isolating said cochlear responses from other responses.

* * * * *